(12) United States Patent
LaHaye

(10) Patent No.: US 6,569,153 B1
(45) Date of Patent: May 27, 2003

(54) MULTI-FUNCTION SURGICAL INSTRUMENT FOR FACILITATING OPHTHALMIC LASER SURGERY

(76) Inventor: Leon C. LaHaye, 566 Sand Pit Rd., Arnaudville, LA (US) 70512

( * ) Notice: Subject to any disclaimer, the term of this patent is extended or adjusted under 35 U.S.C. 154(b) by 0 days.

(21) Appl. No.: 09/960,582

(22) Filed: Sep. 21, 2001

Related U.S. Application Data

(63) Continuation-in-part of application No. 09/894,264, filed on Jun. 28, 2001.

(51) Int. Cl.$^7$ ............................................. A61B 18/18
(52) U.S. Cl. ............................. 606/4; 606/5; 606/166; 604/294; 604/300
(58) Field of Search .................. 606/4–6, 166; 607/88–92; 604/294–298, 300–316

(56) References Cited

U.S. PATENT DOCUMENTS

| | | | | |
|---|---|---|---|---|
| 5,108,412 A | * | 4/1992 | Krumeich et al. | 606/166 |
| 5,941,873 A | * | 8/1999 | Korenfeld | 606/1 |
| 5,980,543 A | * | 11/1999 | Carriazo et al. | 606/166 |
| 6,344,040 B1 | * | 2/2002 | Juhasz et al. | 606/4 |

* cited by examiner

Primary Examiner—Linda C. M. Dvorak
Assistant Examiner—Ahmed M Farah
(74) Attorney, Agent, or Firm—Joseph L. Lemoine, Jr.

(57) ABSTRACT

A multi-function surgical instrument for facilitating ophthalmic surgery of the eye by laser means. Included are a lower ring and an upper ring. One or two intermediate rings may also be included. The lower ring includes a central aperture to capture the limbus and aid in positioning of the eye. Protuberances on the lower surface of said ring, application of vacuum between the lower surface of the ring and the eye, or both may be used to more firmly grip the eye. Ports disposed on the upper surface of the lower ring and connected to a vacuum source may be used to control hydration of the surgical field. Attached to and extending above the upper surface of the lower ring is a sterile platform for reposing temporarily removed tissues during the administration of laser pulses to other tissues. The upper ring is disposed above the surgical bed. Ports disposed along said upper ring and connected to a vacuum source may be used to control smoke and splatters resulting from the ablative procedure and create additional airflow to further control hydration of the surgical field. One, or two, intermediate rings, proximate the upper ring, may be employed to dispense irrigating liquids, gases such as air or oxygen, or both liquids and gases as may be desired onto open tissues of the eye proximate to the lower ring below.

18 Claims, 4 Drawing Sheets

(Section 1-1)

MULTI-FUNCTION SURGICAL INSTRUMENT FOR FACILITATING OPHTHALMIC LASER SURGERY

This patent application is a continuation-in-part application of presently pending U.S. patent application Ser. No. 09/894,264 filed Jun. 28, 2001.

The new matter disclosed and claimed herein relates to disclosure of two additional rings, one of which may be used to dispense liquids, and the other which may be used to dispense gas, onto opened tissues of the eye during ophthalmic surgery.

FIELD OF THE INVENTION

In the field of ophthalmic surgery the use of lasers is well known. In laser assisted in-situ kerotomileusis pulses of laser light are used to ablate desired portions of the stromal bed following temporary removal of the outer tissues of the cornea. After replacement of the temporarily removed tissues the cornea is reshaped. During such procedure, and other ophthalmic procedures involving ablation of eye tissue, positioning and fixation of the eye against movement is important, as is proper tissue hydration, control of smoke, plume and splatter, maintaining cleanliness of open tissues, etc. The invention disclosed and claimed herein relates to a multifunction instrument placed on the surface of the eye during ablative eye surgery to assist the ophthalmic surgeon to perform laser ablative eye surgery.

BACKGROUND OF THE INVENTION

In corneal surgery the use of lasers is well known. In such procedures precisely controlled pulses of laser light are used to remove thin layers of tissue by ablation. For instance, in photorefractive keratectomy ("PRK") the cornea is reshaped by first removing the epithelium and Bowman's layer (by various means) and ablating the stromal bed by laser (after which the epithelium and Bowman's layer are left to re-form by healing). In laser assisted in-situ kerotomileusis ("LASIK") the cornea is reshaped by temporarily removing the outer layers (epithelium, Bowman's layer and a portion of the stromal bed) thereof by sharp instrument, ablating selected areas of the underlying stromal bed by laser and then replacement of the removed tissues. Various other corneal surgery is also performed using a laser to ablatively remove selected eye tissue.

These procedures encounter some common challenges. The eye must be positioned properly, and fixed against movement therefrom, so that the laser pulses are applied, consistently, to only the selected tissues. Ablation of eye tissue creates airborne smoke, plume and splatter which can cause subsequent laser pulses to be applied non-uniformly and other adverse effects. Ablation of over-lying tissue can result in non-uniform or excess hydration of the underlying tissue which can result in total, partial and possibly non-uniform underdosage. Migration of exterior liquids into the surgical field can not only mask subsequent treatment, but can also increase the risk of infection or other contaminants.

In addition, in LASIK there are issues regarding placement of the temporarily removed tissues during administration of the laser pulses. To facilitate exact replacement of temporarily removed tissues to their original position at the conclusion of the surgery, they are typically not entirely removed at the beginning of the procedure, but rather left attached by a "hinge" of tissue (forming what is commonly called a corneal "flap"). During ablation this "flap" is typically folded over onto the sclera, where it is exposed to eye liquids, debris from ablated tissue, bacteria and other undesirable materials. In such position there is also the risk that excess eye liquids may float the flap into the laser field where it may be damaged. There is also a risk of damage to this sensitive flap during handling to replace it over the stromal bed.

Other art discloses ophthalmic tools which includes some, but not all, of the features of the multifunction tool herein disclosed and claimed. For instance U.S. Pat. No. 5,108,412 to Rosenbaum et al discloses a suction ring for attachment to the sclera in the limbus plane. This apparatus is used to guide a trepan perpendicularly to the limbus plane. In U.S. Pat. No. 5,980,543 to Carriazo et al a similar suction ring is used to guide a microkeratome parallel to the limbus. In neither of these patents is the suction ring used to fix the position of the eye in relation to a laser or structure not attached to the ring. In neither of these patents does the suction ring include a platform for "storage" and replacement of a corneal flap during a surgical procedure. In neither of these patents are other attributes of the invention, such as plume and splatter evacuation means, means for creating flow of dehydrating gas over the aperture of the ring, means for improved irrigation for a surgical field, etc., disclosed.

Likewise U.S. Pat. Nos. 5,941, 873 and 5,971,977 to Korenfeld shows one, but not other, attributes of the invention disclosed and claimed herein. In these patents there is disclosed a device having a ring-shaped tube with a plurality of apertures disposed about the inner circumference thereof, to aid in smoke, plume and splatter removal during an ablative procedure of the eye. These patents do not teach any structure for aspirating liquid away from an open stromal bed nor do they teach a sterile platform on which to repose a corneal flap during an ablative procedure of the eye.

The invention disclosed and claimed herein is a multi-function surgical instrument directed to each of the above-mentioned issues. It provides a means for fixing the position of the eye, as may be required, during surgery. It provides a means for controlling hydration of open and/or ablated eye tissue during surgery. It provides a means to aspirate liquids containing ablative debris from the surgical field. It provides a means to prevent potentially contaminated liquids from migrating from outside to the inside of the surgical field.

Also provided is a sterile platform, elevated above potentially contaminating liquids, upon which to repose a corneal flap (and protect it from smoke, plume and splatter) during surgery. The invention disclosed also provides means for removing smoke, plume and splatter resulting from ablation of tissue. Thus the invention disclosed and claimed herein is directed not only to more uniform and consistent application of laser pulses (by establishing good fixation of the eye, removing excess hydration, smoke, plume and splatter from the surgical field) but better protects open and/or ablated tissue from contaminating debris and/or bacteria.

DESCRIPTION OF THE PREFERRED EMBODIMENT OF THE INVENTION

While the present invention will be described with reference to preferred embodiments, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. It is therefore intended that the present invention not be limited to the particular embodiments disclosed herein, but that the invention will include all embodiments (and legal equivalents thereof) falling within the scope of the appended claims.

Figure 1:
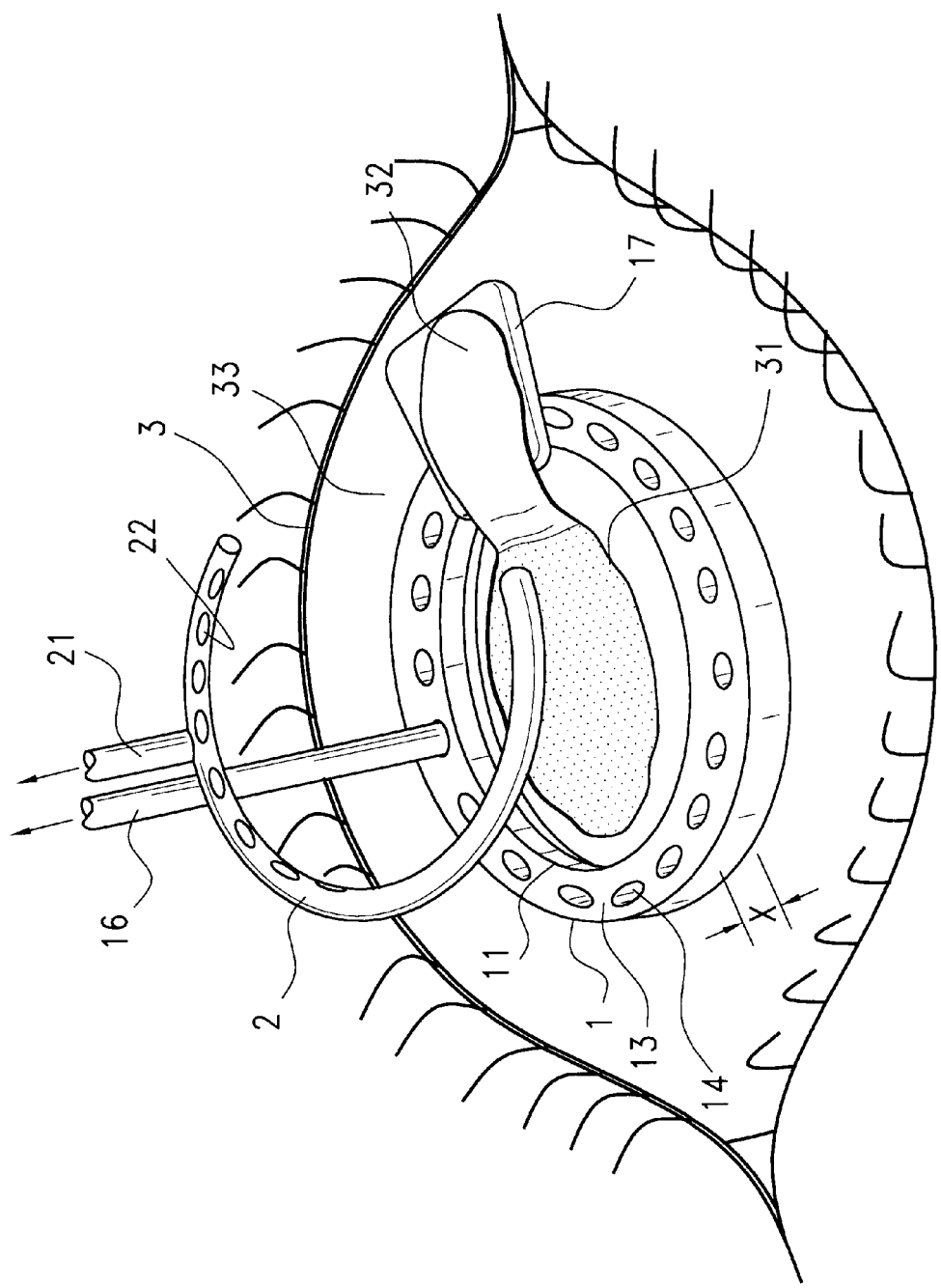
FIG. 1 is a perspective view of the preferred embodiment of the disclosed and claimed invention in the preferred, nasal, position on a patient's eye with an open stromal bed.
Figure 1A:
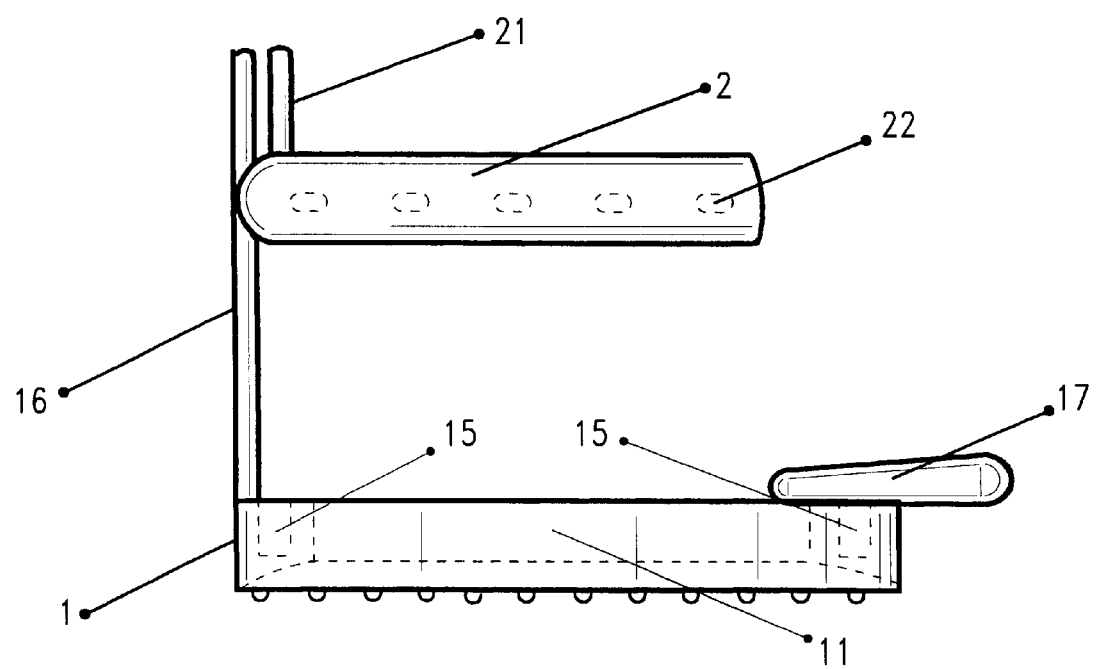
FIG. 1a is an elevational view of an embodiment of the invention shown in FIG. 1. is

FIG. 1 is a schematic view of the preferred embodiment of the surgical instrument of the present invention in position on a human eye 3. FIG 1a depicts the instrument of FIG. 1 in elevational view. Shown are two generally ring-shaped structures, lower ring 1 and upper ring 2, the structure and purpose of which will be herein described in enabling detail.

Figure 2:
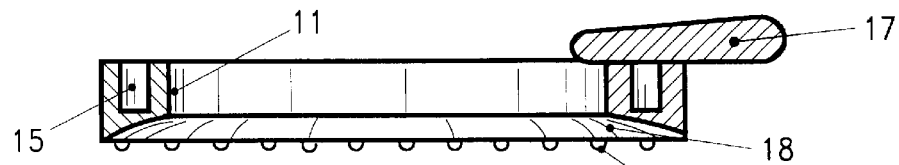
FIG. 2 is a perspective view of the lower surface of the lower ring of an alternative embodiment of the present invention.

Lower ring 1 has several functions. Its central aperture 11 is sized approximately that of the circumference of the limbus, thus "capturing" the corneal bulge of the eye. This tends to fix the position of the eye with respect to the ring. Thus by fixing the position of lower ring 1 the surgeon is able to fix the position of the eye itself. Even more firm fixation of lower ring 1 to the eye may be accomplished by other means, such as application of a vacuum between the eye 3 and the lower surface 18 of said ring, or by set of protuberances 19, such as shown in FIG. 2 on the lower surface of said ring. Thus by controlling the position of lower ring 1 the surgeon may firmly fix the position of the eye as he or she may find required.

Figure 3A:
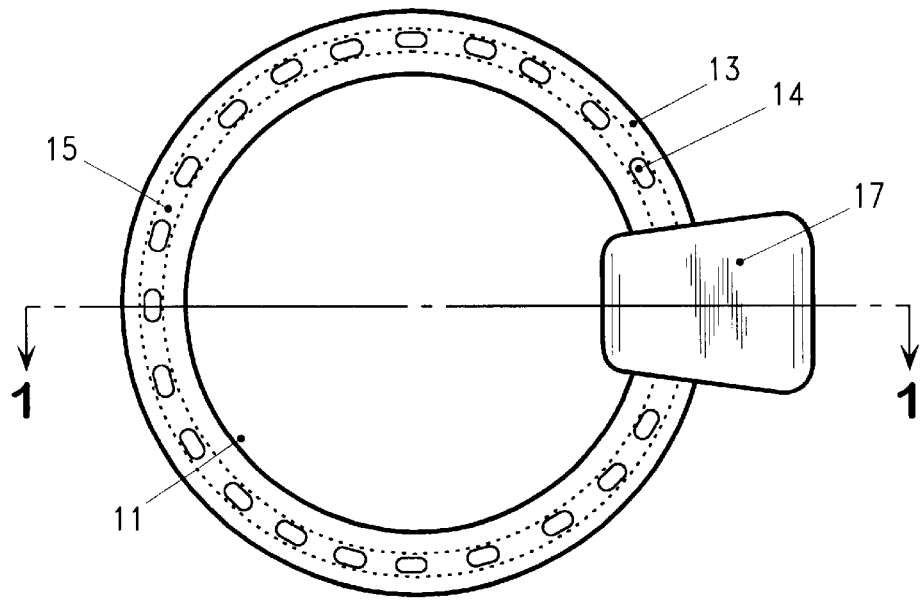
FIG. 3a is an elevational view of the lower ring of the preferred embodiment of the present invention.
Figure 3B:
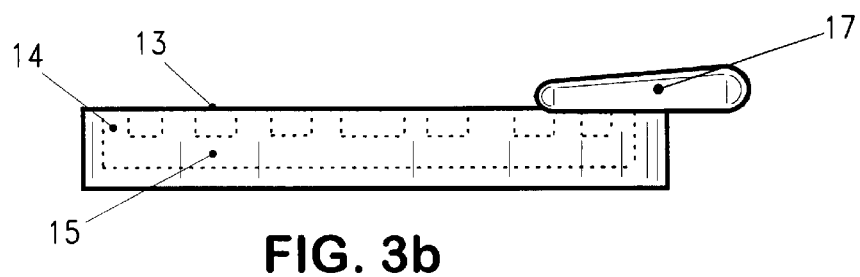
FIG. 3b is a top plan view of the lower ring of the preferred embodiment of the present invention.

Lower ring 1 also provides means to control hydration of the eye tissues which have been opened and/or are being ablated by laser. For example, referring to FIG. 1, in LASIK an open stromal bed 31 is created by removal of corneal flap 32 (by folding said flap onto platform 17). The height of lower ring 1, represented by dimension X, is such that the upper surface 13 of said ring is at, or preferably slightly below, the upper surface of tissues being ablated (which in LASIK will be stromal bed 31); so that excess liquids from or on said tissues tend to flow radially outward and onto upper surface 13 of said ring. The upper surface of said ring may also be inclined radially downward from its inner circumference to aid flow of liquid in a radially outward direction. As said liquids flow onto upper surface 13 of lower ring 1 they will tend to be aspirated into ports 14 disposed in the upper surface 13 of lower ring 1. As is shown in FIG. 3 ports 14 are interconnected by annular passageway 15 disposed within lower ring 1. Said passage-way is connected to vacuum means by tube 16. In addition to aspirating excess liquids from stromal bed 31, the flow of air into ports 14 tends to create a flow of air over said stromal bed. This passage of air tends to remove excess liquids by evaporation. Thus by controlling the intensity of the vacuum applied to tube 16 the surgeon can control hydration of stromal bed 31. The size of ports 14 may increase in proportion to increased distance from tube 16 so as to cause the flow of air to be more uniform about the circumference of lower ring 1.

In the preferred embodiment of the invention, lower ring 1 is also provided with platform 17, which may be permanently or removably attached to upper surface 13 or lower ring 1. This platform not only provides a place to repose the corneal flap 32 (thus keep it off of sclera 33) during application of laser pulses, but also facilitates return of corneal flap 32 to the stromal bed 31 at the conclusion of the surgery. In the preferred embodiment the surfaces of platform 17 are smooth and curved so as to prevent any tearing or sticking of said flap. During application of laser pulses to the stromal bed 31 the corneal flap 32 may be covered with a wet, sterile sponge (not shown) to protect the flap from debris from ablated tissue. In the preferred embodiment the upper surface of platform 17 has a plurality of grooves to facilitate the introduction of liquid between the corneal flap and the platform (thus facilitate "floating" of the flap off of the platform at the conclusion of the surgery).

The primary function of upper ring 2 is to remove smoke, plume and splatter from the surgical field, but it also enhances air flow over the surgical field to help control excess hydration. In the preferred embodiment upper ring 2 may be a generally circular length of rigid tubing, connected to vacuum means attached to tube 21. Ports 22 extend through the wall of said ring. While other dispositions of ports 22 is comprehended by the invention (such as ports disposed about the outer circumference, at the bottom or top of the tubing) in the preferred embodiment of the invention ports 22 are disposed facing radially inward, on the inner circumference of said tubing. As above, said ports may increase in size in proportion to increased distance from tube 21 in order to produce a more uniform airflow around the ring. Increasing intensity of the vacuum applied to the tube 21 increases air flow and enhances removal of smoke, plume and splatter.

While upper ring 2 may constitute a full circle (and this embodiment is comprehended by the invention), in the preferred embodiment upper ring 2 does not constitute a full circle, but is only a segment thereof having closed ends, which does not extend above platform 17 (so as to facilitate access to platform 17 by the surgeon).

In most cases upper ring 2 will be disposed approximately 3–30 millimeters above upper surface 13 of lower ring 1. There it may be attached to tube 16 or to a handle or separate frame (not shown) which is also attached to lower ring 1. Upper ring 2 may be attached to a fixed position on any of said structures, or it may be slidably disposed thereon in the direction to and from lower ring 1 (so that the distance between lower ring 1 and upper ring 2 may be varied as circumstances may require). Upper ring 2 may also be made removably attached to any of said structures, so that the surgeon can remove it when desired.

Figure 4A:
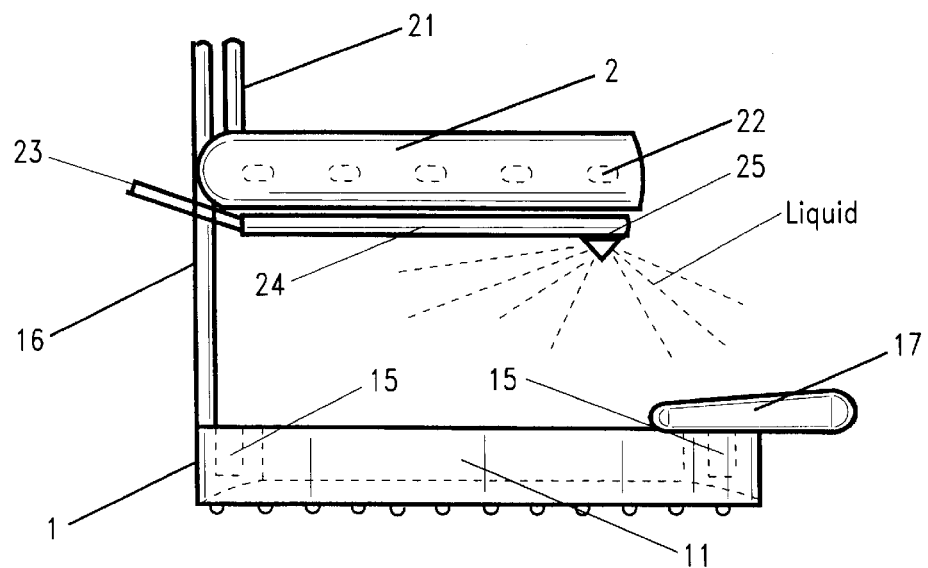
FIG. 4a is an elevational view of an alternative embodiment of the present invention.

Shown in FIG. 4a, is an alternative embodiment of the invention disclosed and claimed. This embodiment may be equipped with means to dispense a liquid onto the surgical bed. While it may be used at other times, this feature of the invention has particular utility to wash debris from the stromal bed and the exposed underside of the corneal flap following completion of ablative procedures, but before return of the corneal flap to the stromal bed. In the preferred embodiment of this alternative liquid is fed through port 23 to semi-circular tube 24 disposed below lower ring 2. Alternatively semi-circular tube 24 may be disposed above, outside of, inside of or within lower ring 2. From semi-circular tube 24 liquid may be sprayed from nozzle 25 when desired. Preferably nozzle 25 is above the edges of platform 17, as is shown in FIG. 4a, to facilitate the spraying of liquid onto the underside of corneal flap 32, as it lays exposed on platform 17, and facilitate spray of liquid onto the exposed stromal bed 31 as well. However other positioning of nozzles 25 are comprehended by the invention, its essence being to be able to dispense irrigation liquids downward, from lower ring 2, onto open tissues of the cornea, prior to closure of said tissues.

Figure 4B:
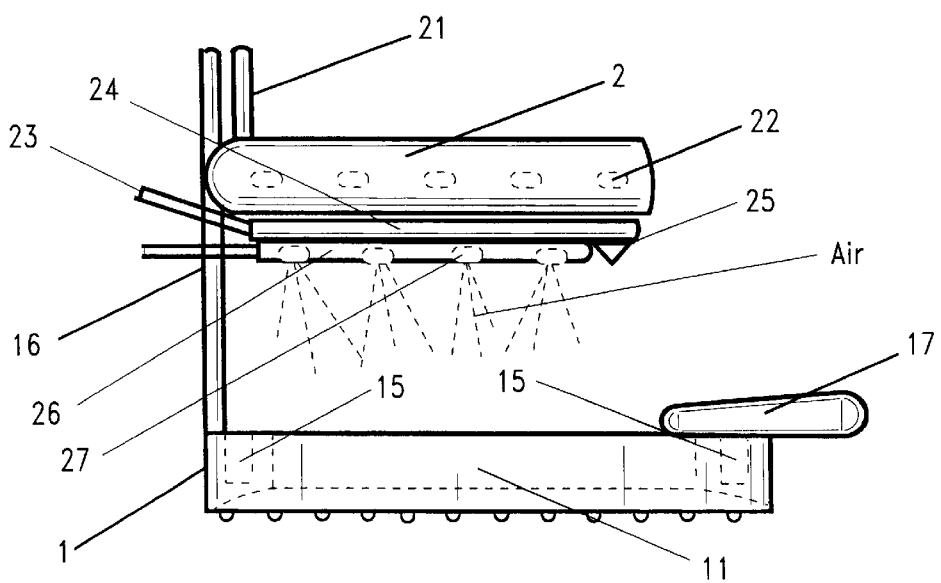
FIG. 4b is an elevational view of another alternative embodiment of the present invention.

In yet another embodiment of the invention, shown in FIG. 4b, lower ring 2 may also be equipped with means to blow a gas, such as oxygen, air or such other gas as may be desired, onto the open stromal bed 31 of the eye, as may be desired or required. As suggested earlier, during ablation of the stromal bed 31, excessive and uneven hydration of the stromal bed can and does occur, and cause subsequent application of laser energy to be unevenly applied. This is, of course, undesirable. Accordingly an alternative embodiment of the invention may include means to blow a, preferably dry and sterile, gas onto the stromal bed 31 to reduce hydration of the tissues of said bed. Blowing of said gas will also aid in removal of smoke, plume and splatter, and gas such as oxygen may have a beneficial effect on said tissues. In this alternative the gas is directed downwardly and toward the center of aperture 11. As shown in FIG. 4b this may be accomplished by a semi-circular tube 26 having closed ends which is disposed below ring 2 and has a plurality of ports 27 which are directed towards the stromal bed 31. In other embodiments gas may be routed to ports 27 by passageway contained above, outside of, inside of or within lower ring 2, the essence of this embodiment of the invention being to provide a means, for use in combination with the other attributes of the invention, to blow a gas onto stromal bed 31 when the ophthalmic surgeon believes that doing so will be efficacious during corneal surgery of the eye.

The preferred embodiment of the invention is preferably used with platform 17 disposed nasally, as it is easiest to form the corneal flap 32 with a nasal hinge. But it may be rotatably disposed about the limbus as the particular surgeon may prefer. It will be typically applied to the eye after creation of a corneal flap (typically by microkeratome). After application of the instrument to the eye, the corneal flap will typically be lifted, directly from the stromal bed, onto platform 17, which is sterile. Disposed on platform 17 the corneal flap may be draped with a wet, surgical sponge or other sterile covering to protect it from tissue debris resulting from ablation to follow. Following this, the surgeon will typically apply a desired amount of vacuum to lower ring 1 and upper ring 2, and then use the instrument to fix the position of the eye as required during application of laser pulses. In the simplest form fixing the position of the eye may be by means of the surgeon holding the instrument of the present invention in place with another instrument or by handle attached to the instrument of the present invention, but other forms of positioning mechanisms, including magnetic means, may also be utilized. During the ablative procedure the surgeon may adjust the intensity of vacuum on one or both rings, as he may find effective to control hydration of the stromal bed and remove smoke, plume and splatter caused by ablation. At the conclusion of the ablative procedure the stromal bed and other tissues of the eye will typically be thoroughly rinsed to remove ablated tissue and other debris thereon. Typically vacuum will be left on lower ring 1 during rinsing to help remove debris containing liquids from the stromal bed and help prevent debris containing liquid from outside of the surgical field from entering the stromal bed. Following thorough rinsing of the eye (including the corneal flap), the corneal flap will be typically "floated" back into place by application of liquids. Floating of the corneal flap back into place may be accomplished with the instrument of the present invention in place, or as the instrument is lifted from the eye (in which case the instrument to itself can be used to guide the flap back over the stromal bed, and is therefore preferred).

It is thus to be appreciated that apparatus in accordance with the principles and teachings of the present inventive disclosure constitutes an advancement in the field of art to which the invention pertains. While the above description contains certain specificities, these should not be construed as limitations on the scope of the invention, but rather as an exemplification of preferred embodiments thereof. Accordingly, the scope of the present invention should be determined not by the embodiments illustrated, but by the appended claims and their legal equivalents.

What is claimed is:

1. A surgical instrument, for placement around the limbus of the eye during corneal surgery by laser, comprising:

a. a lower ring having a vertical axis, an upper surface and lower surface spaced axially apart and defining a thickness therebetween, and an outer diameter and inner diameter spaced radially apart and defining an annularwall therebetween, all together defining a disc shaped structure having a central aperture surrounded by an annular wall;

b. wherein the inner diameter of said lower ring is sized to fit closely about the circumference of the limbus of the eye;

c. wherein said lower ring includes a platform superposed on a section of said upper surface and extending a height thereabove;

d. an upper ring, spaced vertically above said lower ring when said lower ring is positioned on the surface of the eye around the limbus thereof, said upper ring having an internal gas transmissible passage-way, a plurality of gas transmissible ports extending between the exterior surface of said upper ring and said gas transmissible passage-way and a gas transmissible port extending between said gas transmissible passage-way and an external vacuum source; and, e. an intermediate ring, spaced between said lower ring and said upper ring, said intermediate ring having an internal liquid transmissible passage-way, a plurality of liquid transmissible ports extending between the exterior surface of said intermediate ring and said liquid transmissible passage-way and a liquid transmissible port extending between said liquid transmissible passage-way and an external liquid source.

2. The surgical instrument of claim 1, wherein the plurality of liquid transmissible ports extending between the exterior surface of said intermediate ring and said liquid transmissible passage-way are directed towards the central aperture of said lower ring.

3. The surgical instrument of claim 1, wherein the plurality of liquid transmissible ports extending between the exterior surface of said intermediate ring and said liquid transmissible passage-way are directed towards the platform superposed on a section of said upper surface of said lower ring.

4. The surgical instrument of claim 1, wherein said intermediate ring is spaced apart from said lower ring.

5. The surgical instrument of claim 4, wherein said intermediate ring is spaced proximately to said upper ring.

6. The surgical instrument of claim 1, wherein a portion of the plurality of the liquid transmissible ports extending between the exterior surface of said intermediate ring and said liquid transmissible passage-way are directed towards the platform superposed on a section of said upper surface of said lower ring and another portion of said plurality of liquid transmissible ports extending between the exterior surface of said intermediate ring and said liquid transmissible passage-way are directed towards the central aperture of said lower ring.

7. The surgical instrument of claim 6, wherein said intermediate ring is spaced apart from said lower ring.

8. The surgical instrument of claim 7, wherein said intermediate ring is spaced proximately to said upper ring.

9. The surgical instrument of claim 1, further comprising a second intermediate ring, spaced between said lower ring and said upper ring, said second intermediate ring having an internal gas transmissible passage-way, a plurality of gas transmissible ports extending between the exterior surface of said intermediate ring and said gas transmissible passage-way and a gas transmissible port extending between said gas transmissible passage-way and an external gas source.

10. The surgical instrument of claim 9, wherein said second intermediate ring is spaced apart from said lower ring.

11. The surgical instrument of claim 9, wherein said second intermediate ring is spaced proximately to said upper ring.

12. The surgical instrument of claim 9, wherein the plurality of gas transmissible ports extending between the exterior surface of said intermediate ring and said gas transmissible passage-way are directed towards the central aperture of said lower ring.

13. The surgical instrument of claim 12, wherein said second intermediate ring is spaced apart from said lower ring.

14. The surgical instrument of claim 12, wherein said second intermediate ring is spaced proximately to said upper ring.

15. A surgical instrument, for placement around the limbus of the eye during corneal surgery by laser, comprising:
   a. a lower ring having a vertical axis, an upper surface and lower surface spaced axially apart and defining a thickness therebetween, and an outer diameter and inner diameter spaced radially apart and defining an annular wall therebetween, all together defining a disc shaped structure having a central aperture surrounded by an annular wall;
   b. wherein the inner diameter of said lower ring is sized to fit closely about the circumference of the limbus of the eye;
   c. wherein said lower ring includes a platform superposed on a section of said upper surface and extending a height thereabove;
   d. an upper ring, spaced vertically above said lower ring when said lower ring is positioned on the surface of the eye around the limbus thereof, said upper ring having an internal gas transmissible passage-way, a plurality of gas transmissible ports extending between the exterior surface of said upper ring and said gas transmissible passage-way and a gas transmissible port extending between said gas transmissible passage-way and an external vacuum source; and,
   e. an intermediate ring, spaced between said lower ring and said upper ring, said intermediate ring having an internal gas transmissible passage-way, a plurality of gas transmissible ports extending between the exterior surface of said intermediate ring and said gas transmissible passage-way and a gas transmissible port extending between said gas transmissible passage-way and an external gas source.

16. The surgical instrument of claim 9, wherein the plurality of gas transmissible ports extending between the exterior surface of said intermediate ring and said gas transmissible passage-way are directed towards the central aperture of said lower ring.

17. The surgical instrument of claim 15, wherein said intermediate ring is spaced apart from said lower ring.

18. The surgical instrument of claim 17, wherein said intermediate ring is spaced proximately to said upper ring.

* * * * *